(12) United States Patent
Kinast

(10) Patent No.: US 11,213,424 B2
(45) Date of Patent: Jan. 4, 2022

(54) EYE DROP DISPENSEMENT AID

(71) Applicant: BEDO SOLUTIONS, LLC, Portland, OR (US)

(72) Inventor: Robert Kinast, Portland, OR (US)

(73) Assignee: Bedo Solutions, LLC, Portland, OR (US)

( * ) Notice: Subject to any disclaimer, the term of this patent is extended or adjusted under 35 U.S.C. 154(b) by 373 days.

(21) Appl. No.: 15/749,093

(22) PCT Filed: Jul. 27, 2016

(86) PCT No.: PCT/US2016/044328
§ 371 (c)(1),
(2) Date: Jan. 30, 2018

(87) PCT Pub. No.: WO2017/023653
PCT Pub. Date: Feb. 9, 2017

(65) Prior Publication Data
US 2018/0221203 A1    Aug. 9, 2018

Related U.S. Application Data

(60) Provisional application No. 62/199,795, filed on Jul. 31, 2015, provisional application No. 62/287,874, filed on Jan. 27, 2016.

(51) Int. Cl.
*A61F 9/00* (2006.01)
*A61M 35/00* (2006.01)
(52) U.S. Cl.
CPC .......... *A61F 9/0026* (2013.01); *A61M 35/00* (2013.01)

(58) Field of Classification Search
CPC ................................................ A61F 9/0026
See application file for complete search history.

(56) References Cited

U.S. PATENT DOCUMENTS

| 2,482,431 | A | | 9/1949 | Okawa |
| 2,676,592 | A | | 4/1954 | Wood |
| 2,722,216 | A | * | 11/1955 | Robbins ................ A61F 9/0026 604/302 |

(Continued)

FOREIGN PATENT DOCUMENTS

| WO | 9640025 | 12/1996 |
| WO | WO 1996/040025 A1 | 12/1996 |

(Continued)

OTHER PUBLICATIONS

"Evaluating eye drop instillation technique in glaucoma patients," by Gupta R., et al., Journal of Glaucoma, 2012, vol. 21, pp. 189-192.

(Continued)

*Primary Examiner* — Tatyana Zalukaeva
*Assistant Examiner* — Heather K Barnwell
(74) *Attorney, Agent, or Firm* — Klarquist Sparkman, LLP

(57) ABSTRACT

An aid for dispensing eye drops to improve adherence. The aid, which may be integrated into an eye drop bottle (10) or be separately attached, aligns the eye drop container to better dispense eye drops, while resting the engagement surface (55) of an alignment structure (50) upon the bridge of a user's nose (80), supporting the eye drop container and not intruding upon the temporal half of the field of view of the user's eye.

17 Claims, 3 Drawing Sheets

(56) References Cited

U.S. PATENT DOCUMENTS

| | | |
|---|---|---|
| 2,898,911 A | 8/1959 | Seymour |
| 3,446,209 A | 5/1969 | Macha |
| 3,521,636 A | 7/1970 | Mahoney et al. |
| 3,872,865 A | 3/1975 | Casey |
| 4,085,750 A | 4/1978 | Bosshold |
| 4,134,403 A * | 1/1979 | Johnsen .............. A61F 9/0026 222/192 |
| 4,392,590 A | 7/1983 | Hofmann-Igl |
| 4,471,890 A | 9/1984 | Dougherty |
| 4,531,944 A | 7/1985 | Bechtle |
| 4,733,802 A | 3/1988 | Sheldon |
| 4,834,727 A | 5/1989 | Cope |
| 4,960,407 A | 10/1990 | Cope |
| 5,059,188 A | 10/1991 | Goddard |
| 5,569,224 A | 10/1996 | Michalos |
| 5,578,019 A | 11/1996 | Feldman |
| 5,713,495 A * | 2/1998 | Menard ............... A61F 9/0026 222/212 |
| 5,836,911 A | 11/1998 | Marzynski |
| 5,902,292 A | 5/1999 | Feldman |
| 6,010,488 A | 1/2000 | Deas |
| 6,149,625 A | 11/2000 | Weston et al. |
| 6,258,059 B1 | 7/2001 | Weston et al. |
| 6,595,970 B1 | 7/2003 | Davidian |
| 6,632,202 B1 | 10/2003 | Hagele |
| 7,235,065 B1 | 6/2007 | Sorensen |
| 7,309,329 B2 | 12/2007 | Cress |
| 7,527,613 B2 | 5/2009 | Gaynes |
| 8,206,362 B1 | 6/2012 | Crosswell, Jr. |
| 8,216,195 B2 | 7/2012 | Wu |
| 8,348,912 B2 | 1/2013 | Rehkemper et al. |
| 8,734,408 B2 | 5/2014 | Marx |
| 9,033,941 B2 | 5/2015 | Rehkemper et al. |
| 9,072,581 B1 | 7/2015 | Alam |
| 9,486,356 B2 | 11/2016 | Agnew et al. |
| 2009/0259204 A1* | 10/2009 | Galdeti ............... A61F 9/0026 604/302 |
| 2010/0160872 A1 | 6/2010 | Harrison |
| 2010/0174248 A1 | 7/2010 | Wu |
| 2010/0286634 A1 | 11/2010 | Marx |
| 2012/0150132 A1* | 6/2012 | Cress .................. A61F 9/0026 604/290 |
| 2014/0171884 A1 | 6/2014 | Rehkemper et al. |
| 2014/0257206 A1 | 9/2014 | Fateh |
| 2014/0371688 A1* | 12/2014 | Rezaei Abbassi .... A61F 9/0026 604/290 |
| 2015/0088099 A1* | 3/2015 | Lorch ................. A61F 9/0026 604/521 |
| 2015/0173945 A1* | 6/2015 | Fateh .................. A61F 9/0026 604/300 |
| 2015/0313757 A1 | 11/2015 | Agnew et al. |

FOREIGN PATENT DOCUMENTS

| | | |
|---|---|---|
| WO | 9727834 | 8/1997 |
| WO | WO 1997/027834 A1 | 8/1997 |
| WO | 0218942 | 3/2002 |

OTHER PUBLICATIONS

"Aids for Eye Drop Administration," by Isiah Davies, et al., Survey of Ophthalmology, vol. 62, No. 3, 2017, pp. 332-345.

Evaluation of the efficacy and safety of a new device for eye drops instillation in patients with glaucoma, by Daniela Junqueira, et al., Clinical Ophthalmology, vol. 2015:9, 2015, pp. 367-371.

"Xal-Ease®: impact of an ocular hypotensive device on ease of eyedrop administration, patient compliance, and satisfaction," by Jean-Philippe Nordmann, et al., European Journal of Ophthalmology vol. 19, No. 6, 2009, pp. 949-956.

"Evaluation of an eye drop guide to aid self-administration by patients experience with topical use of glaucoma medication," by Asif Salyani, MD, et al., Canadian Journal of Ophthalmology, vol. 40, No. 2, 2005, pp. 170-174.

"The psychological impact of eyedrops administration in children," by Sujuan, Jane Lim, et al., Journal of the AAPOS, vol. 19, No. 4, Aug. 2015, pp. 338-343.

"Container Closure Systems for Packaging Human Drugs and Biologies," Chemistry Manufacturing, and Controls Documentation, U.S. Dept. of Health and Human Services, Food and Drug Administration, May 1999, pp. 1-41, A-1 to E-2.

"Role of Opticare Eye Drop Delivery System in Patients with Rheumatoid Arthritis," by Henry Averns, et al., The Journal of Rheumatology 1999, 26:12, pp. 2615-2618.

"A Video Study of Drop Instillation in Both Glaucoma and Retina Patients with Visual Impairment," by Amy L. Hennessy, et al., American Journal of Ophthalmology, vol. 152, No. 6, Dec. 2011, pp. 982-988.

"Methods for Self-Administration of Eyedrops," by Charles E. Letocha, MD, Ann Ophthalmol, vol. 17, 1985, pp. 768-769.

"An Objective Evaluation of Eyedrop Instillation in Patients With Glaucoma," by Jennifer Stone, et al., Archives of Ophthalmology. vol. 127, No. 6, 2009, pp. 732-736.

"Eye drop instillation technique in patients with glaucoma," by AJ Tatham et al., Eye. vol. 27, 2013, pp. 1293-1298.

"Videographic Assessment of Glaucoma Drop Instillation," by Gabriel Lazcano-Gomez, et al., Journal of Current Glaucoma Practice, vol. 9, No. 2, 2015, pp. 47-50.

"Evaluation of eye drop administration technique in patients with glaucoma or ocular hypertension," by Gail F. Schwarz, et al., Current Medical Research & Opinion, vol. 29, No. 11, 2013, pp. 1515-1522.

"Improper topical self-administration of ocular medication among patients with glaucoma," by Melissa M. Brown, et al., Canadian Journal of Ophthalmology, vol. 19, No. 1, 1984, pp. 2-5.

"Comparison of Eye Drop Instillation Before and After Use of Drop Application Strips in Glaucoma Patients on Chronic Topical Therapy," by Reetika Sharma, et al., Journal of Glaucoma, vol. 25, No. 4, 2016, pp. 438-440.

"Evaluation of the Xal-Ease™ latanoprost delivery system," by Leo Semes, et al., Optometry, vol. 28, 2007, pp. 30-33.

"Mirror-hat device as a drop delivery aid: A pilot study," by M. Hermina Strungaru et al., Canadian Journal of Ophthalmology, vol. 49, No. 4, 2014, pp. 333-338.

"Ophthalmic Dose Compliance Monitor," by Arinne Lyman, et al., University of Wisconsin—Madison, Oct. 19, 2005, pp. 1-22.

* cited by examiner

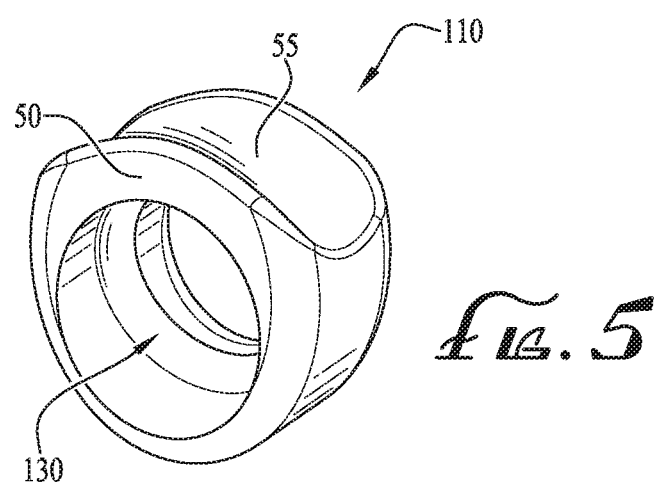
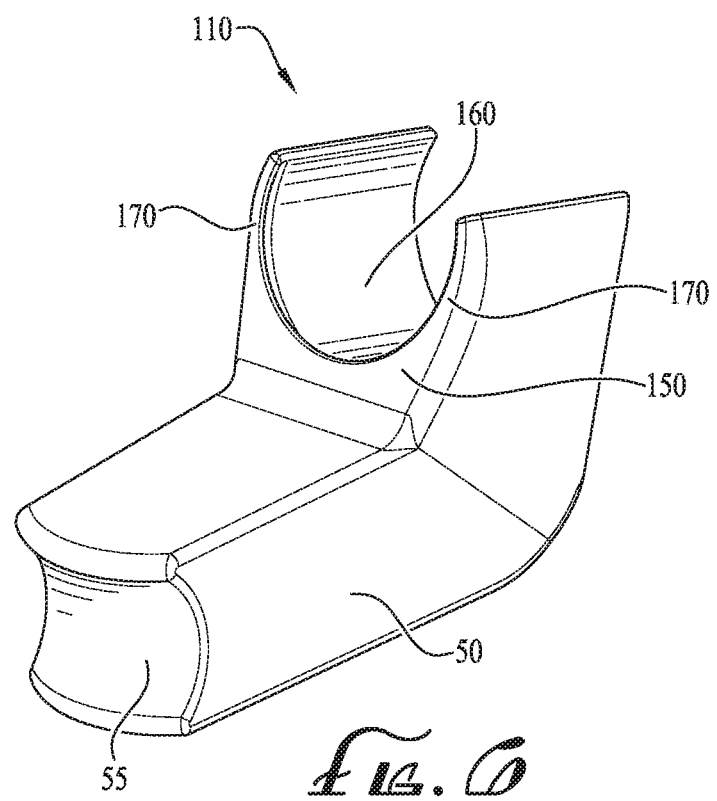

EYE DROP DISPENSEMENT AID

CROSS REFERENCE TO RELATED APPLICATION

This application claims the benefit under 35 U.S.C. § 119(e) of U.S. Provisional Application Ser. No. 62/199,795, filed on 31 Jul. 2015 and of U.S. Provisional Application Ser. No. 62/287,874, filed on 27 Jan. 2016, the contents of which are incorporated herein by reference in their entirety.

FIELD OF THE INVENTION

The present invention relates, generally, to devices and methods for delivery of medication and improving the rate of successful medication adherence. More particularly, the present invention relates to improving the rate of successful delivery of medication in the form of eye drops from an eye drop bottle to an eye.

BACKGROUND

A number of conditions, including glaucoma, conjunctivitis and allergies may be treated by the use of eye drops. Eye drops may contain steroids, antihistamines, antibiotics. prostaglandin analogs, beta blockers, alpha agonists, carbonic anhydrase inhibitors, or other drugs. Additionally, eye drops may be used to lubricate the eye or replace tears. In order for the treatment with eye drops to be effective, good adherence to treatment, i.e., remembering to use the eye drop and getting sufficient amount of the eye drop into the eye, is needed. Some adherence studies of glaucoma patients indicate that approximately 45% of patients demonstrate poor ability to remember to use their eye drops, and other studies show that when patients do attempt to administer eye drops, they frequently miss the eye.

One reason for poor adherence is the inability to successfully administer an eye drop. Patients may accidentally miss the eye instead placing the drop on the eyelids or cheek, or they may touch the bottle tip against the ocular surface causing contamination of the bottle and possible ocular surface damage. In a recent study, over 30% of patients missed the eye while attempting to instill an eye drop and over 75% touched the bottle tip to the ocular surface or eyelids. Only 10% of patients exhibited proper technique. See e.g., Gupta R, Patil B, Shaw B M, "Evaluating eye drop instillation technique in glaucoma patients," *Journal of Glaucoma*, 2012, 21: 189-92. Correctly placing an eye drop through conventional means is challenging.

Researchers and eye care providers have had difficulty developing a suitable device to improve the success rate of instilling eye drops. Existing eye drop delivery devices have not been widely adopted due to their difficulty of use, intimidating nature, and lack of efficacy. Unsuccessful attempts to address these problems which may be examples of prior art are: U.S. Published Patent Appl'ns Nos. US2010-160872, US2010-174248, US2010-286634, US2012-150132, and US2014-371688; U.S. Pat. Nos. 2,482,431; 2,676,592; 2,898,911; 3,446,209; 3,521,636; 3,872,865; 4,085,750; 4,471,890; 4,531,944; 4,733,802; 4,834,727; 4,960,407; 5,059,188; 5,569,224; 5,578,019; 5,836,911; 5,902,292; 6,010,488; 6,149,625; 6,258,059; 6,595,970; 7,235,065; 8,206,362; 8,216,195; 8,734,408; 8,348,912; 9,033,941; and 9,072,581; European Patent Publ'ns EP0013187A1 and E00934921; and WIPO Publ'ns WO/1996/040025A1, and WO/1997/027834A1.

A successful device for instilling eye drops would either incorporate a reservoir for holding eye drops or affix securely to a single use or multi-use eye drop bottle and have a surface that fits firmly against the upper nose/bridge of the nose/nasion area avoiding contact with the eyelids and orbital rim and periocular tissues and eyebrow. The bottle or reservoir would be supported on the nose and pivot the eye drop bottle downward towards the ocular surface so that the bottle tip would be above the surface without touching it, permitting the dispensing tip to hover over the eye but avoiding having any substantial portion of the device, other than the dispensing tip itself, crossing over the eye to intrude upon the temporal field of view of the eye. Additionally, a successful device for improving eye drop adherence would also include the ability to monitor adherence and alert when medication is due, through the inclusion of electronics for this function.

BRIEF DESCRIPTION OF THE DRAWINGS

The features, aspects and advantages of the present invention will become better understood with regard to the following description, appended claims and accompanying figures wherein:

FIG. 5 illustrates an embodiment of a holder for an eye drop bottle in ring form.

FIG. 6 illustrates an embodiment of a holder for an eye drop bottle using a partially encircling clasp structure.

DETAILED DESCRIPTION

Figure 1:
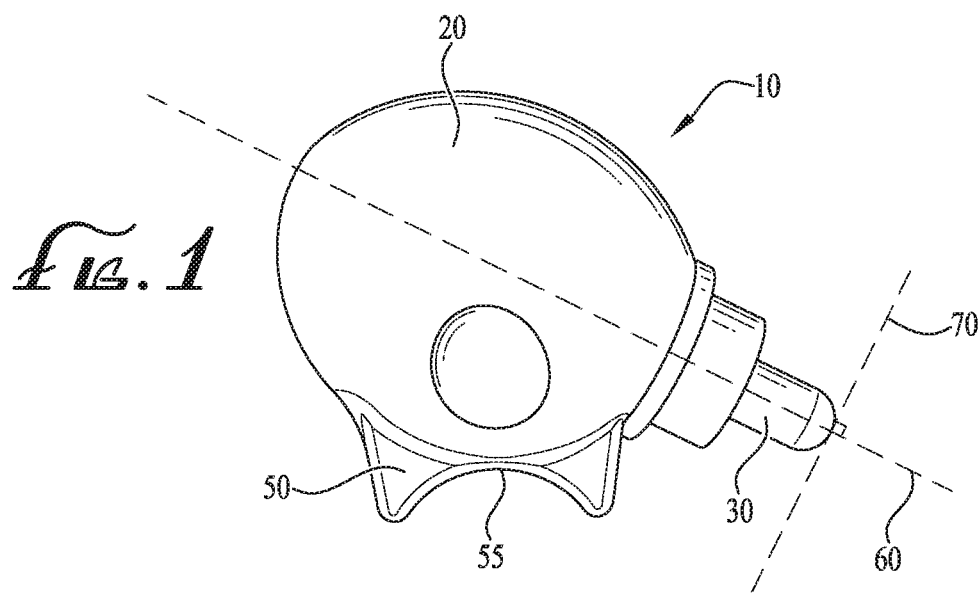
FIG. 1 illustrates an embodiment of an eye drop bottle.

In the following description of the preferred embodiments, reference is made to the accompanying drawings which show by way of illustration specific embodiments in which the invention may be practiced. Wherever possible, the same reference numbers will be used throughout the drawings to refer to the same or like parts. It is to be understood that other embodiments may be utilized and structural and functional changes may be made without departing from the scope of the present invention. It is to be understood that as used herein, the directional term medial means toward the line of symmetry of the human body and the directional term lateral means away from the line of symmetry of the human body. Similarly when referring to the field of view of an eye, the nasal field of view extends medially from a vertical plane aligned with the directly forward looking line of sight of the eye and the temporal field of view extends laterally from the same vertical plane.

A number of conditions, including glaucoma, allergies, and dryness may be treated by the use of eye drops. Eye drops may contain steroids, antihistamines, antibiotics. prostaglandin analogs, beta blockers, alpha agonists, carbonic anhydrase inhibitors, or other drugs. Additionally, eye drops may be used to lubricate the eye or replace tears. In order for the treatment with eye drops to be effective, good adherence to treatment, i.e., remembering to use the eye drops and getting sufficient amount of the eye drop into they eye, is needed.

Approximately 45% of glaucoma patients demonstrate poor ability to remember to use their eye drops (defined as using less than 75% of expected eye drop doses) and about 30% of glaucoma patients miss the eye while administering the eye drops. Poor adherence increases the risk of blindness in patients with glaucoma. In addition to glaucoma treatment, medication adherence affects all eye diseases treated with topical drops, whether antibiotics for a conical ulcer or steroids for uveitis.

Successfully administering eye drops presents many challenges including dexterity difficulties, complex spatial orientation, and patient fear. Successfully administering an eye drop requires that the bottle tip remain in precise position over the globe without contacting the ocular surface while applying force to the bottle. This complex task is a challenge for all patients, especially the elderly and those with a tremor or arthritis. Patients are often fearful of contact with the eyes, which can make drop instillation more difficult.

Because of these issues, researchers and eye care providers have had difficulty developing a suitable device to improve the success rate of instilling eye drops. Prior devices have included large, clunky, awkward, and/or unstable aspects that fit over the entire globe or touch the eyelids or orbital rim or eyebrow or are prone to movement around the eye. Devices that touch periocular tissues and are visible over the eye can intimidate patients and limit adoption.

The invention provides for a secure, stable, easily manipulated, eye drop delivery device which does not block or impede upon the temporal field-of-view of the user's eye, when the user is applying eye drops. FIG. 1 illustrates an embodiment of the invention integrated into an eye drop bottle 10, the bottle comprises a reservoir 20, a tip 30 through which the eye drops are delivered. A cap, not shown, that allows the bottle to be securely closed, and an alignment structure 50, which includes an engagement surface 55 that may take the form of an anchor or footplate. For purposes of this description, the primary axis 60 of the bottle is an axis extending through the center of the tip 30, perpendicular to the face 70 of the tip 30. Although illustrated as an integrated unit, it would be obvious to a person of ordinary skill in the art that the reservoir 20 and tip 30 could be manufactured so as to be detachable from alignment structure 50 via a mechanical or other connections, such as pieces which snap together, use a mechanical fastener, use an adhesive affixment, or use Velcro®, for example. This would allow, for example, for a single use reservoir 20 and tip 30, with a re-usable alignment structure. It would also be obvious to a person of ordinary skill in the artthat the reservoir 20 and tip 30 and alignment 50 structure could take the form of various dimensions, shapes, sizes, and configurations; for example, two tips could be included on opposing sides of the reservoir 20 to allow simultaneous bilateral eye drop delivery.

Figure 2:
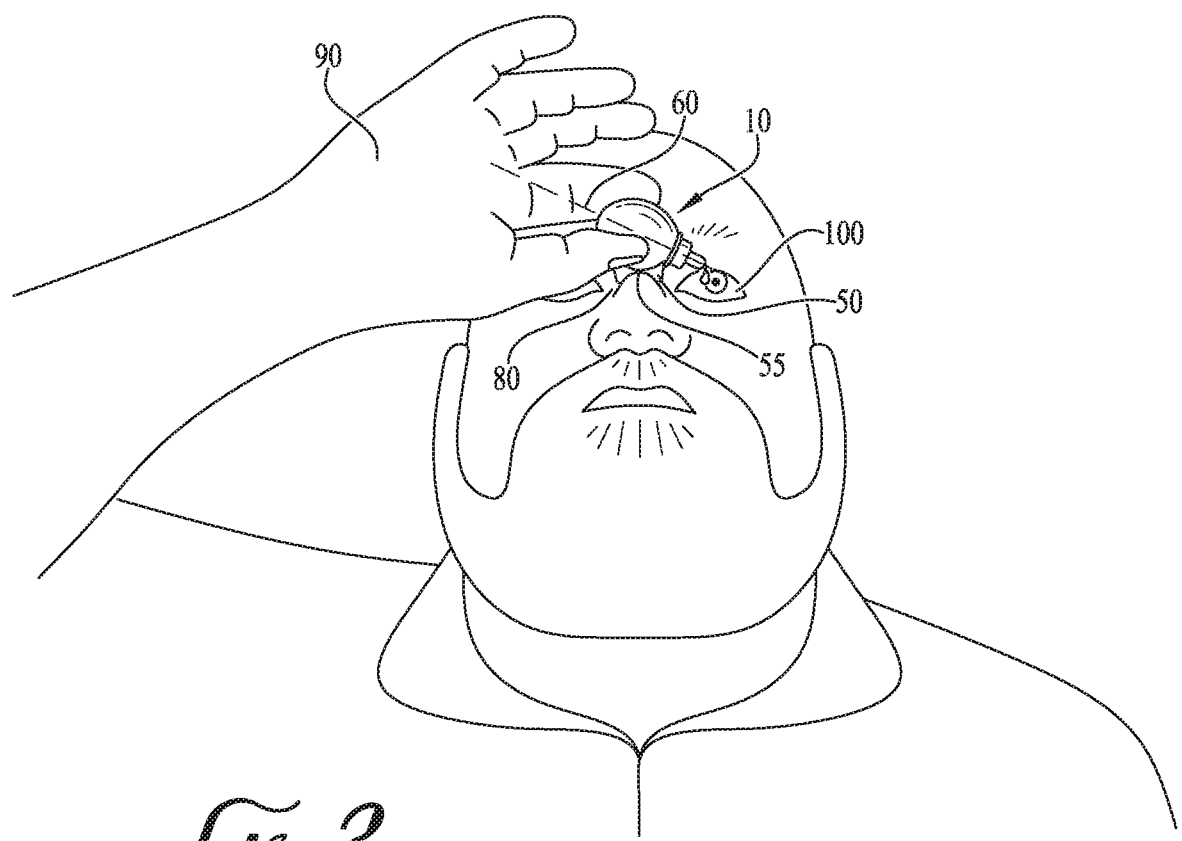
FIG. 2 illustrates use of an eye drop bottle from FIG. 1.

The use of the bottle 10 is illustrated in FIG. 2. An engagement surface 55 of the alignment structure 50 is securely placed against the bridge of the user's nose 80, which as used herein throughout refers to the general area of the upper or mid-nose and lower forehead proximate to the nasal bones and glabella area. The tip 30 of the bottle 10 is then rotated about the engagement surface 55 into position over the user's eye 100. The bottle rests on the bridge of the user's nose 80 and is stabilized by the user's hand 90, which may also squeeze the bottle 10 to administer the eye drops through the tip 30. Because the primary axis 60 of the bottle 10 is rotated medially from the forward line of sight of the user, the bottle 10 does not approach the eye directly along, or parallel to, the forward line of sight of the user's eye 100. Thus, neither the user's hand 90 nor the body of the bottle 10 (i.e., the portion of the bottle 10 excluding the tip 30), extend into the temporal half of the field of view of the user's eye 100, and the application method incites less consternation and anxiety in users, as users are accustomed, when focusing closely, to have an obstruction in the nasal half of their field of view, i.e., their nose, but are not typically accustomed to obstructions directly in their forward line of sight or in the temporal half of their field of view.

Fear or anxiety regarding the application of eye drops can result in lack of cooperation in the application of eye drops and directly affect the efficacy of treatment, especially in children. See Sujuan, Jane Lim, et al., "The psychological impact of eye drops administration in children," *Journal of the AAPOS*, Vol. 19, No. 4, August 2015, pp. 338-343. Decreasing or ameliorating this anxiety by avoiding intrusions into the temporal half of the field of view or along the forward line of sight of the user's eye provides significant benefit.

In the United States, the Food and Drug Administration regulates packaging for medical eye drops. See, e.g., "Container Closure Systems for Packaging Human Drugs and Biologics," Chemistry Manufacturing, and Controls Documentation, U.S. Dept. of Health and Human Services, Food and Drug Administration, May 1999. The present invention, when embodied in an eye drop bottle would be able to meet any suitability requirements, including those relating to protection, safety, compatibility, and performance, as well as quality control and stability requirements. Additionally, any bottle would need to be approved by the FDA for the specific medication it will contain because of concerns regarding sterility, drop quantity, and drop volume. It would be clear to a person of ordinary skill in the art that specific changes to the materials used in the manufacture, adoption of specific dimensions and features for the tip and any cap affixed to the tip for sealing the bottle can be made in the implementation of a bottle in accord with the invention.

Figure 3:
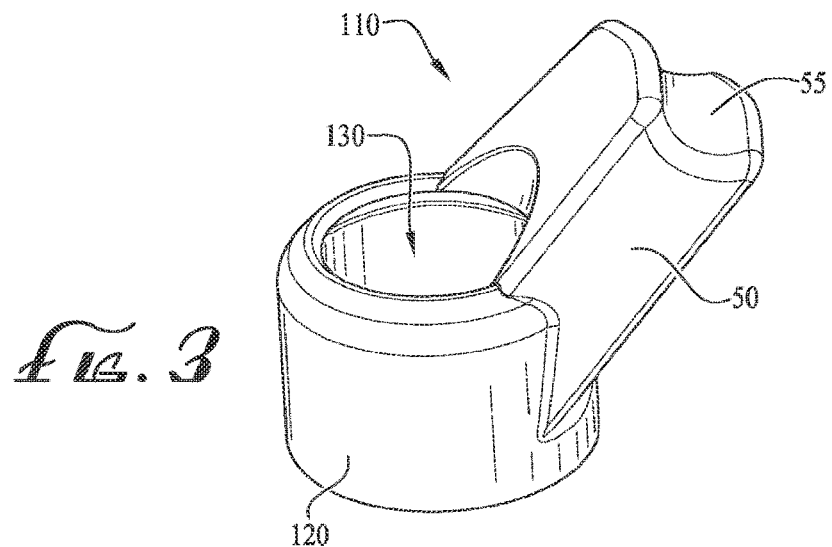
FIG. 3 illustrates an embodiment as a holder for an eye drop bottle.

FIG. 3 illustrates an embodiment of the present invention as a holder 110 for use with a standard pre-existing single or multi-use ophthalmic drop container also known as an eye drop container or bottle. The holder 110 comprises a sheath 120 which slides over the drop container (not shown). The cap and tip of the bottle pass through an opening 130 in the holder 110, such that the holder 110 is affixed to the drop container by friction. The holder further comprises an alignment structure 50 that includes an engagement surface 55.

Figure 4:
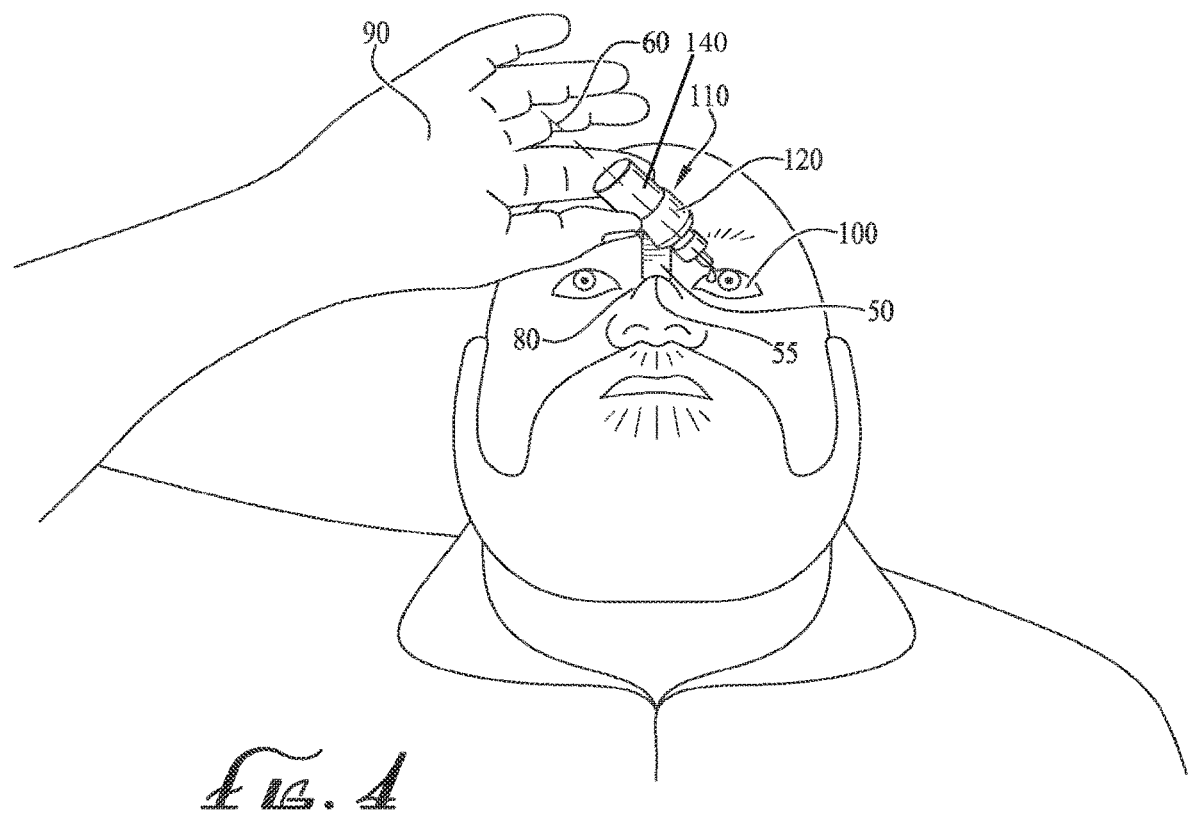
FIG. 4 illustrates use of a holder as in FIG. 3, with an inserted conventional eye drop bottle.

The use of the holder 110 is illustrated in FIG. 4. An engagement surface 55 of the alignment structure 50 is securely placed against the bridge of the user's nose 80. The container 140 and the holder 110 are rotated about the engagement surface 55 to put the tip of the container 140 over the user's eye 100. The holder 110, with the pre-existing single or multi-use ophthalmic drop container 140, rests on the bridge of the user's nose 80 and is stabilized by the user's hand 90, which may also squeeze the container 140 to administer the eye drops through the tip 30 and directly into the user's eye. Because the eye drops do not come in contact with the holder 110, the holder 110 cannot contaminate the eye drops and it is appropriate for use with multi-use drop containers 140, as well as single use containers 140. The container 140 may be squeezed outside of the area covered by the sheath 120 or the sheath 120 may be made of a flexible material that allows for the container 140 to be squeezed in conjunction with the sheath 120. Because the primary axis 60 of the container 140 is rotated medially from the forward line of sight of the user, the body of the container 140 (the portion of the container 140 excluding the tip 30), the holder 110, and the user's hand 90 do not extend into the temporal half of the field of view of the user's eye 100.

An embodiment of a holder 110 in the form of a ring is illustrated in FIG. 5. The ring includes a central opening 130 through which a single or multi-use ophthalmic drop container may be inserted. The container is securely held within the holder 110 by a friction fit. The holder further comprises an alignment structure 50 having an engagement surface 55. When in use, the engagement surface 55 is placed firmly against the bridge of the user's nose and the tip of the ophthalmic drop container is rotated about the engagement surface 55 to position the tip of the container above the user's eye.

An embodiment of a holder 110 that uses a clasping structure 150 to affix securely to a standard pre-existing single or multi-use ophthalmic drop container (not shown) is illustrated in FIG. 6. The clasping structure 150 includes an opening 160 which allows the arms 170 of the clasping structure 150 to flex sufficiently to allow an ophthalmic drop container (not shown) to pass through the opening 160. The ophthalmic drop container is held in place against the clasping structure 150 by friction resulting from the inward force of the arms 170 on the container, although it would be obvious to a one of ordinary skill in the art that other mechanisms to firmly affix the ophthalmic drop container to the clasping structure 150 are possible, such as a tension member or spring clamp affixed to the arms 170 of the clasping structure 150, which encompass at least portion of the circumference of the standard pre-existing ophthalmic drop container and hold the ophthalmic drop container in place against the clasping structure 150, or other mechanisms that applies compressive force against the pre-existing ophthalmic drop container to hold it firmly in place against the clamping structure 150. The holder further comprises an alignment structure 50 having an engagement surface 55. When in use, the engagement surface 55 is placed firmly against the bridge of the user's nose and the tip of the ophthalmic drop container is rotated about the engagement surface 55 to position the tip of the container above the user's eye.

A further feature of the present invention is the ability to incorporate an adherence auditing mechanism which can detect when the ophthalmic eye drop are being administered, and optionally, in what amount. This mechanism can take the form of electronics which is contained within the invention, optionally, within the alignment structure 50, which can detect when an eye drop is being administered, track and share adherence data, and alert when an eye drop medication is due.

Although there are several oral pill bottle devices with excellent adherence monitoring mechanisms, such as the AdhereTech, Vitality GlowCap, and SMRxT devices, similar devices for eye drop bottles are not currently available. Eye drop bottles present additional challenges because each unique eye drop bottle requires an FDA-approved closure. Further, current eye drop bottles do not include the physical space or intrinsic capacity for an adherence monitoring mechanism. The only eye drop monitor currently available on the market is the Travatan Dosing Aid, a large, bulky device which fits only one brand of eye drop and requires pressing on a physical lever to measure adherence. The alignment structure 50 permits room for electronics in both the holder 110 and bottle 20, and the adjacent positioning of the eye drop bottle 10 cap to the electronics 50 can permit a mechanical or non-mechanical counting mechanism while still permitting a watertight FDA approved closure.

It would be obvious to one of ordinary skill in the art that there are numerous ways to identify and detect administration. These include monitoring, via optical, mechanical, electronic or magnetic sensors, when the cap is removed from and/or attached to the bottle 10 or the pre-existing multi-use eye drop container 140, or when an eye drop exits the bottle tip 30 or passes by a sensor. This may also include sensors to detect when the bottle 10 or pre-existing multi-use eye drop container is squeezed to dispense eye drops. Accuracy of such detection may be improved by position sensors which can confirm the orientation of the bottle or pre-exiting ophthalmic eye drop container. The adherence auditing mechanism may also include recording the date, time, and duration, of use and may include communications capabilities such as through Wi-Fi, Bluetooth®, or other wireless communications protocols to communicate the monitoring data to other devices. These devices and methods for identifying and detecting administration would generally be applicable whether the invention is implemented as an eye drop bottle 10 with an alignment structure 50 or as a holder 110 for use with a pre-existing ophthalmic drop container.

There is disclosed in the above description and the drawings, an eye drop bottle and holder system with an alignment structure that fully and effectively overcomes the disadvantages associated with the prior art. However, it will be apparent that variations and modifications of the disclosed embodiments may be made without departing from the principles of the invention. The presentation of the preferred embodiments herein is offered by way of example only and not limitation, with a true scope and spirit of the invention being indicated by the following claims.

Any element in a claim that does not explicitly state "means" for performing a specified function or "step" for performing a specified function, should not be interpreted as a "means" or "step" clause as specified in 35 U.S.C. § 112.

What is claimed is:

1. An alignment aid for an eye drop container comprising:
   a bridge support portion comprising a curved engagement surface configured to contact a bridge of a user's nose;
   a container-receiving portion configured to receive the eye drop container in a fixed; non-vertical orientation relative to the bridge support portion when the bridge support portion is in a horizontal orientation; and
   an extending portion extending between the engagement surface to the container-receiving portion,
   wherein the container-receiving portion is spaced apart from the engagement surface by the extending portion, and the extending portion is configured to space away a dispensing tip of the eye drop container from the bridge of the user's nose;
   wherein the extending portion, when the bridge support portion is in use in the horizontal orientation, extends away from the bridge of the user's nose perpendicularly to a horizontal plane defined by the bridge support portion.

2. The alignment aid of claim 1, wherein the container-receiving portion is positioned at an angle relative to the horizontal plane defined by the bridge support portion.

3. The alignment aid of claim 1, wherein the container-receiving portion comprises a ring that at least partially encircles the eye drop container.

4. The alignment aid of claim 1, wherein the container-receiving portion comprises a sheath engaging an exterior of the eye drop container.

5. The alignment aid of claim 1, wherein container-receiving portion comprises a gripping mechanism that grips an exterior of the eye drop container.

6. The alignment aid of claim 5, wherein the gripping mechanism is a spring clamp.

7. The alignment aid of claim 5, wherein the gripping mechanism is a circumferential retention tension element.

8. The alignment aid of claim 5, wherein the gripping mechanism comprises a compression element that provides compression pressure against the eye drop container.

9. An alignment aid for an eye drop container comprising:
- a bridge support member comprising a longitudinally-extending body having a first end and a second end, the first end including a curved engagement surface configured to contact a bridge of a user's nose; and
- a sheath coupled to the second end of the longitudinally-extending body and configured to receive the eye drop container in a non-vertical orientation when the bridge support portion is in a horizontal orientation, the sheath being spaced apart from the bridge of the user's nose by the longitudinally-extending body of the bridge support member,
- wherein the longitudinally-extending body is configured to space away a dispensing tip of the eye drop container from the bridge of the user's nose.

10. The alignment aid of claim 9, wherein the sheath is configured to slide over a body portion of the eye drop container.

11. The alignment aid of claim 9, wherein the sheath has a cylindrical shape.

12. The alignment aid of claim 9, wherein the sheath attaches to at least a portion of the eye drop container by a friction fit.

13. The alignment aid of claim 9, wherein the sheath is formed from a flexible material.

14. The alignment aid of claim 9, wherein an opening in the sheath is positioned at an angle relative to a horizontal plane defined by the engagement surface of the bridge support member.

15. A method for dispensing eye drops from an eye drop container having a container body and a dispensing tip comprising:
- providing an alignment aid with a container-receiving portion spaced apart from a bridge support portion by a longitudinally-extending body;
- attaching the eye drop container to the container-receiving portion of the alignment aid so that a primary axis of the eye drop container is in a non-vertical orientation when the bridge support portion is in a horizontal orientation;
- positioning a curved engagement surface of the bridge support portion of the alignment aid in contact with a bridge of a user's nose;
- rotating the eye drop container about the engagement surface to align an opening of the dispensing tip of the eye drop container in a desired position above a user's eye; and
- engaging the eye drop container to dispense eye drops from the eye drop container into the user's eye while the dispensing tip of the eye drop container is spaced away from the bridge of the user's nose by the longitudinally-extending body.

16. The method of claim 15, wherein the container-receiving portion comprises a sheath and attaching the eye drop container to the container-receiving portion comprises moving the sheath over the container body.

17. The method of claim 15, wherein the container-receiving portion comprises a pair of arms that form a clasping structure and the act of attaching the eye drop container to the container-receiving portion comprises engaging the pair of arms with a body portion of the eye drop container.

\* \* \* \* \*